United States Patent
McLawhorn

(10) Patent No.: US 9,526,570 B2
(45) Date of Patent: Dec. 27, 2016

(54) TISSUE CUTTING CAP

(71) Applicant: Cook Medical Technologies LLC, Bloomington, IN (US)

(72) Inventor: Tyler E. McLawhorn, Winston-Salem, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 236 days.

(21) Appl. No.: 14/039,699

(22) Filed: Sep. 27, 2013

(65) Prior Publication Data
US 2014/0100570 A1 Apr. 10, 2014

Related U.S. Application Data
(60) Provisional application No. 61/709,455, filed on Oct. 4, 2012.

(51) Int. Cl.
*A61B 18/14* (2006.01)
*A61B 18/00* (2006.01)

(52) U.S. Cl.
CPC .. *A61B 18/1485* (2013.01); *A61B 2018/00577* (2013.01); *A61B 2018/00601* (2013.01); *A61B 2018/00982* (2013.01)

(58) Field of Classification Search
CPC ............... A61B 1/00137; A61B 2018/00601; A61B 1/00089; A61B 1/00091; A61B 1/0008
USPC ........................................................ 600/127
See application file for complete search history.

(56) References Cited

U.S. PATENT DOCUMENTS

| | | |
|---|---|---|
| 1,056,336 A | 3/1913 | Hurdman |
| 4,074,718 A | 2/1978 | Morrison, Jr. |
| 4,386,752 A | 6/1983 | Pavlak et al. |
| 4,522,205 A | 6/1985 | Taylor et al. |
| 4,532,924 A | 8/1985 | Auth et al. |
| 4,706,667 A | 11/1987 | Roos |
| 4,765,331 A | 8/1988 | Petruzzi et al. |

(Continued)

FOREIGN PATENT DOCUMENTS

| | | |
|---|---|---|
| JP | 2009 183581 A | 8/2009 |
| WO | WO 98/22184 | 5/1998 |

(Continued)

OTHER PUBLICATIONS

R. Ackroyd et al., "Ablation treatment for Barrett oesophagus: what depth of tissue destruction is needed?," Clin Pathol, 1999;vol. 52, pp. 509-512.

(Continued)

*Primary Examiner* — Jocelyn D Ram
(74) *Attorney, Agent, or Firm* — Brinks Gilson & Lione

(57) ABSTRACT

A tissue cutting cap and a method of delivering energy to a tissue are provided. The tissue cutting cap includes a body having a proximal portion, a distal portion, a distal end, and a lumen extending at least partially therethrough. The tissue cutting cap also includes a cutting portion operably connected to the body where the cutting portion has at least one position where the cutting portion is positioned proximal to the distal end of the body and the cutting portion has a first side, a second side, an end and an opening defined by the first side and the second side. The proximal portion of the body is sized and shaped to fit on a distal end of an endoscope and the distal portion of the body extends distal to the distal end of the endoscope.

14 Claims, 8 Drawing Sheets

(56) References Cited

U.S. PATENT DOCUMENTS

| | | |
|---|---|---|
| 4,823,791 A | 4/1989 | D'Amelio et al. |
| 4,936,842 A | 6/1990 | D'Amelio et al. |
| 5,100,402 A | 3/1992 | Fan |
| 5,197,491 A | 3/1993 | Anderson et al. |
| 5,254,121 A | 10/1993 | Manevitz et al. |
| 5,443,470 A | 8/1995 | Stern et al. |
| 5,454,809 A | 10/1995 | Janssen |
| 5,494,483 A | 2/1996 | Adair |
| 5,514,130 A | 5/1996 | Baker |
| 5,562,703 A | 10/1996 | Desai |
| 5,573,008 A * | 11/1996 | Robinson ............ A61B 10/0266 600/567 |
| 5,575,788 A | 11/1996 | Baker et al. |
| 5,681,282 A | 10/1997 | Eggers et al. |
| 5,683,385 A | 11/1997 | Kortenbach et al. |
| 5,707,355 A | 1/1998 | Zimmon |
| 5,718,702 A | 2/1998 | Edwards |
| 5,743,870 A | 4/1998 | Edwards |
| 5,766,168 A | 6/1998 | Mantell |
| 5,836,906 A | 11/1998 | Edwards |
| 5,906,587 A | 5/1999 | Zimmon |
| 5,925,044 A | 7/1999 | Hofmann et al. |
| 5,957,863 A | 9/1999 | Koblish et al. |
| 5,993,446 A | 11/1999 | Sutter |
| 5,994,717 A | 11/1999 | Igarashi et al. |
| 6,009,877 A | 1/2000 | Edwards |
| 6,015,406 A * | 1/2000 | Goble ................ A61B 18/1485 606/41 |
| 6,027,499 A | 2/2000 | Johnston et al. |
| 6,044,846 A | 4/2000 | Edwards |
| 6,050,993 A | 4/2000 | Tu et al. |
| 6,053,172 A | 4/2000 | Hovda et al. |
| 6,056,744 A | 5/2000 | Edwards |
| 6,059,719 A * | 5/2000 | Yamamoto et al. .......... 600/127 |
| 6,073,052 A | 6/2000 | Zelickson et al. |
| 6,077,257 A | 6/2000 | Edwards et al. |
| 6,086,585 A | 7/2000 | Hovda et al. |
| 6,091,995 A | 7/2000 | Ingle et al. |
| 6,112,123 A | 8/2000 | Kelleher et al. |
| 6,149,647 A | 11/2000 | Tu et al. |
| 6,156,032 A | 12/2000 | Lennox |
| 6,190,381 B1 | 2/2001 | Olsen et al. |
| 6,197,022 B1 | 3/2001 | Baker |
| 6,210,409 B1 | 4/2001 | Ellman et al. |
| 6,231,571 B1 | 5/2001 | Ellman et al. |
| 6,245,067 B1 | 6/2001 | Tu et al. |
| 6,248,081 B1 * | 6/2001 | Nishtalas et al. .............. 600/567 |
| 6,258,084 B1 | 7/2001 | Goldman et al. |
| 6,346,105 B1 | 2/2002 | Tu et al. |
| 6,352,533 B1 | 3/2002 | Ellman et al. |
| 6,355,032 B1 | 3/2002 | Hovda et al. |
| 6,363,937 B1 | 4/2002 | Hovda et al. |
| 6,394,949 B1 * | 5/2002 | Crowley et al. .............. 600/127 |
| 6,402,744 B2 | 6/2002 | Edwards et al. |
| 6,405,732 B2 | 6/2002 | Edwards et al. |
| 6,419,673 B1 | 7/2002 | Edwards et al. |
| 6,464,697 B1 | 10/2002 | Edwards et al. |
| 6,494,881 B1 | 12/2002 | Bales et al. |
| 6,535,764 B2 | 3/2003 | Imran et al. |
| 6,535,768 B1 | 3/2003 | Baker et al. |
| 6,544,261 B2 | 4/2003 | Ellsberry et al. |
| 6,587,731 B1 | 7/2003 | Ingle et al. |
| 6,589,238 B2 | 7/2003 | Edwards et al. |
| 6,591,838 B2 | 7/2003 | Durgin |
| 6,632,193 B1 | 10/2003 | Davison et al. |
| 6,659,106 B1 | 12/2003 | Hovda et al. |
| 6,669,687 B1 | 12/2003 | Saadat |
| 6,685,713 B1 | 2/2004 | Ahmed |
| 6,692,490 B1 | 2/2004 | Edwards |
| 6,712,814 B2 | 3/2004 | Edwards et al. |
| 6,740,082 B2 | 5/2004 | Shadduck |
| 6,746,447 B2 | 6/2004 | Davison et al. |
| 6,763,836 B2 | 7/2004 | Tasto et al. |
| 6,846,312 B2 | 1/2005 | Edwards et al. |
| 6,872,206 B2 | 3/2005 | Edwards et al. |
| 6,918,906 B2 | 7/2005 | Long |
| 6,932,812 B2 | 8/2005 | Crowley et al. |
| 6,994,705 B2 | 2/2006 | Nobis et al. |
| 7,022,105 B1 | 4/2006 | Edwards |
| 7,025,768 B2 | 4/2006 | Elliott |
| 7,097,644 B2 | 8/2006 | Long |
| 7,137,981 B2 | 11/2006 | Long |
| 7,232,438 B2 | 6/2007 | Long |
| 7,252,665 B2 | 8/2007 | Starkebaum et al. |
| 7,344,535 B2 | 3/2008 | Stern et al. |
| 7,347,860 B2 * | 3/2008 | Ouchi ............................ 606/46 |
| 7,442,191 B2 | 10/2008 | Hovda et al. |
| 7,530,979 B2 | 5/2009 | Ganz et al. |
| 7,566,300 B2 | 7/2009 | Devierre et al. |
| 7,648,500 B2 | 1/2010 | Edwards et al. |
| 7,655,004 B2 | 2/2010 | Long |
| 7,658,738 B2 | 2/2010 | Nobis et al. |
| 7,662,151 B2 | 2/2010 | Crompton, Jr. et al. |
| 7,678,069 B1 | 3/2010 | Baker et al. |
| 7,691,101 B2 | 4/2010 | Davison et al. |
| 7,703,459 B2 | 4/2010 | Saadat et al. |
| 7,749,159 B2 | 7/2010 | Crowley et al. |
| 7,758,087 B2 | 7/2010 | Niven et al. |
| 9,204,782 B2 * | 12/2015 | Nguyen ........... A61B 17/32056 |
| 9,216,057 B2 * | 12/2015 | Goshayeshgar ... A61B 18/1492 |
| 2002/0177847 A1 | 11/2002 | Long |
| 2002/0183739 A1 | 12/2002 | Long |
| 2003/0181900 A1 | 9/2003 | Long |
| 2003/0216727 A1 * | 11/2003 | Long ............................... 606/41 |
| 2005/0049454 A1 * | 3/2005 | Ouchi ................ A61B 18/1492 600/105 |
| 2005/0080412 A1 * | 4/2005 | Ouchi ................ A61B 1/00089 606/45 |
| 2006/0167451 A1 | 7/2006 | Cropper |
| 2006/0217698 A1 | 9/2006 | Starkebaum et al. |
| 2007/0203395 A1 * | 8/2007 | Mikkaichi .......... A61B 1/00087 600/127 |
| 2007/0212926 A1 | 9/2007 | Nakaura |
| 2008/0058586 A1 * | 3/2008 | Karpiel ............. A61B 1/00089 600/104 |
| 2008/0103357 A1 * | 5/2008 | Zeiner et al. ................. 600/104 |
| 2008/0200912 A1 | 8/2008 | Long |
| 2008/0242932 A1 | 10/2008 | Carter |
| 2009/0177030 A1 * | 7/2009 | Goto ............................ 600/104 |
| 2009/0221872 A1 | 9/2009 | Liddle et al. |
| 2009/0247823 A1 * | 10/2009 | Yamamoto ......... A61B 18/1492 600/108 |
| 2009/0270856 A1 | 10/2009 | Saadat et al. |
| 2010/0087813 A1 | 4/2010 | Long |
| 2010/0174283 A1 * | 7/2010 | McNall, III ....... A61B 18/1485 606/45 |
| 2010/0256632 A1 | 10/2010 | Crowley et al. |
| 2013/0046138 A1 * | 2/2013 | McLawhorn ...... A61B 1/00087 600/104 |
| 2013/0046300 A1 * | 2/2013 | Binmoeller et al. ............ 606/41 |
| 2016/0106497 A1 * | 4/2016 | Germain ........ A61B 17/320016 606/39 |

FOREIGN PATENT DOCUMENTS

| | | |
|---|---|---|
| WO | WO 99/35987 | 7/1999 |
| WO | WO 00/19926 | 4/2000 |
| WO | WO 01/68015 A1 | 9/2001 |
| WO | WO 2006/122279 A2 | 11/2006 |

OTHER PUBLICATIONS

C. P. Barham et al., "Photothermal laser ablation of Barrett's oesophagus: endoscopic and histological evidence of squamous re-epithelialisation," Gut, 1997, vol. 41, pp. 281-284.

R. M. Bremner et al., "Ultrasonic epithelial ablation of the lower esophagus without stricture formation," Surigical Endoscopy, 1998, vol. 12, pp. 342-347.

Gossner et al., "KTP laser destruction of dysplasia and early cancer in columnar-lined Barrett's esophagus," Gastointestinal Endoscopy, Jan. 1999, vol. 49, Issue 1. pp. 8-12.

(56) References Cited

OTHER PUBLICATIONS

H. Inoue et al., "Endoscopic mucosal resection with a cap-fitted panendoscope for esophagus, stomach, and colon mucosal lesions," Gastrointestinal Endoscopy, 1993 vol. 39, No. 1, pp. 58-62.

Johnston et al., "Endoscopic spray cryotherapy: a new technique for mucosal ablation in the esophagus," Gastrointestinal Endoscopy, Jul. 1999, vol. 50, pp. 86-92.

L. Laine, "Determination of the Optimal Technique for Bipolar Electrocoagulation Treatment," Gastroenterology, 1991, vol. 100, pp. 107-112.

B. Overholt, "Photodynamic therapy for Barrett's esophagus: follow-up in 100 patients," Gastrointestinal Endoscopy, 1999, vol. 49, No. 1, pp. 1-7.

Salo et al., "Treatment of Barrett's Esophagus by Endoscopic Laser Ablation and Antireflux Surgery," Annals of Surgery, vol. 227, No. 1, pp. 40-44.

T. V. Taylor et al., "Ablation of neoplasia by direct current," Br. J. Cancer, 1994, vol. 70, pp. 342-345.

J. van den Boogert, "Photodynamic Therapy for Esophageal Lesions: Selectivity Depends on Wavelength, Power, and Light Dose," The Society of Thoracic Surgeons, Nov. 1999, vol. 68, Issue 5, pp. 1763-1769.

\* cited by examiner

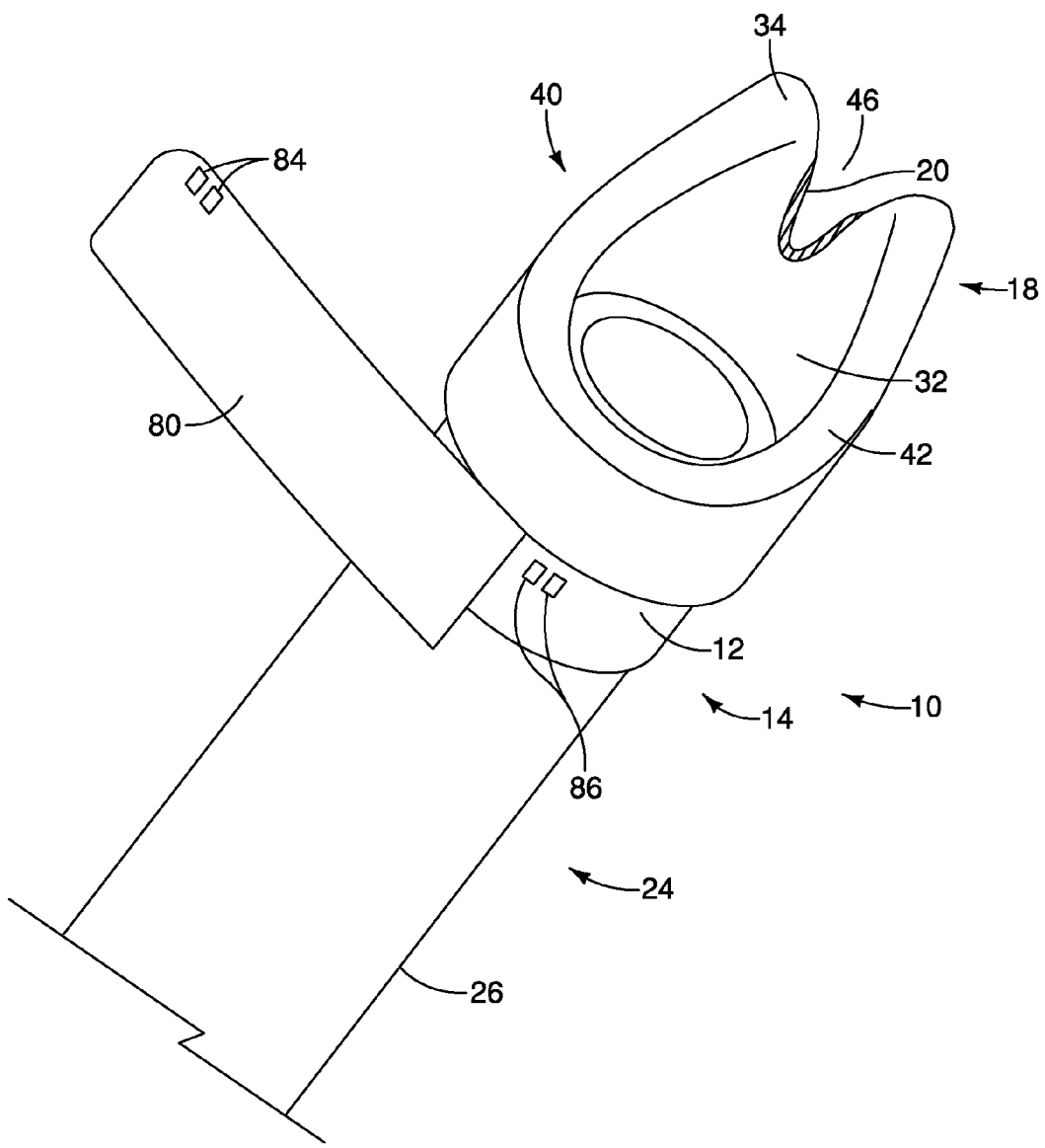
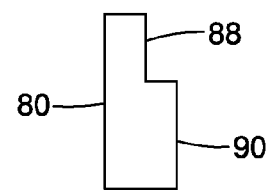
FIG. 3B
FIG. 3C

TISSUE CUTTING CAP

RELATED APPLICATIONS

This application claims the benefit of U.S. Provisional Application No. 61/709,455, filed Oct. 4, 2012, which is incorporated by reference herein in its entirety.

TECHNICAL FIELD

This invention generally relates to medical devices and in particular to an apparatus and method for cutting tissue.

BACKGROUND

Minimally invasive medical procedures are performed in various passageways in the body using elongated instruments inserted through natural orifices or small surgical openings. In some procedures, it is desirable to provide treatment of some diseases using en bloc tissue removal through an elongate device, for example removing tissue lesions or polyps.

In some procedures, such as endoscopic submucosal dissection (ESD), a solution may be submucosally injected between layers of tissue to create a tissue elevation and then electrocautery may be used to cut the margins of the elevated tissue to remove the diseased tissue. Electrocautery devices, such as needle knives, that are currently available all operate in a monopolar fashion through the accessory channel of the endoscope.

One complication associated with the use of monopolar needle knives to excise the tissue is that the tissue may be completely perforated by the electrocautery device rather than excising only specific layers. Currently, advances have been made in limiting the perforations by limiting the use of electrocautery devices to those practitioners with advanced endoscopic skills. Additionally, some devices have been made that include an insulated distal tip to limit the perforations caused by electrocautery devices.

There is a need for an apparatus and a method to provide an electrocautery device that reduces the risk of complications, such as perforations, and allows for cutting of specific layers of tissue. In addition, an electrocautery device that allows for an open accessory channel on an endoscope is advantageous.

BRIEF SUMMARY

Accordingly, it is an object of the present invention to provide a device and a method having features that resolve or improve on one or more of the above-described drawbacks.

In one aspect, a tissue cutting cap is provided. The tissue cutting cap includes a body having a proximal portion, a distal portion, a distal end, and a lumen extending at least partially therethrough. The tissue cutting cap also includes a cutting portion operably connected to the body where the cutting portion has at least one position where the cutting portion is positioned proximal to the distal end of the body and the cutting portion has a first side, a second side, an end and an opening defined by the first side and the second side. The proximal portion of the body is sized and shaped to fit on a distal end of an endoscope and the distal portion of the body extends distal to the distal end of the endoscope.

In another aspect, a method of delivering energy to a tissue site within a patient's lumen using the tissue cutting cap is provided. The method includes positioning the tissue cutting cap within a patient's lumen with the tissue cutting cap positioned on a distal end of an endoscope. The tissue cutting cap includes a body having a proximal portion, a distal portion, a distal end, and a lumen extending at least partially therethrough. The tissue cutting cap also includes a cutting portion operably connected to the body where the cutting portion has at least one position where the cutting portion is positioned proximal to the distal end of the body and the cutting portion has a first side, a second side, an end and an opening defined by the first side and the second side. The method further includes contacting the tissue with the cutting portion, supplying energy to the cutting portion from an energy source and cutting the tissue.

BRIEF DESCRIPTION OF THE DRAWINGS

FIG. 3B is a perspective view of an embodiment of a tissue cutting cap positioned on a distal end of an endoscope using a band;

FIG. 3C is a sectional view through the band shown in FIG. 3B;

DETAILED DESCRIPTION

Figure 1:
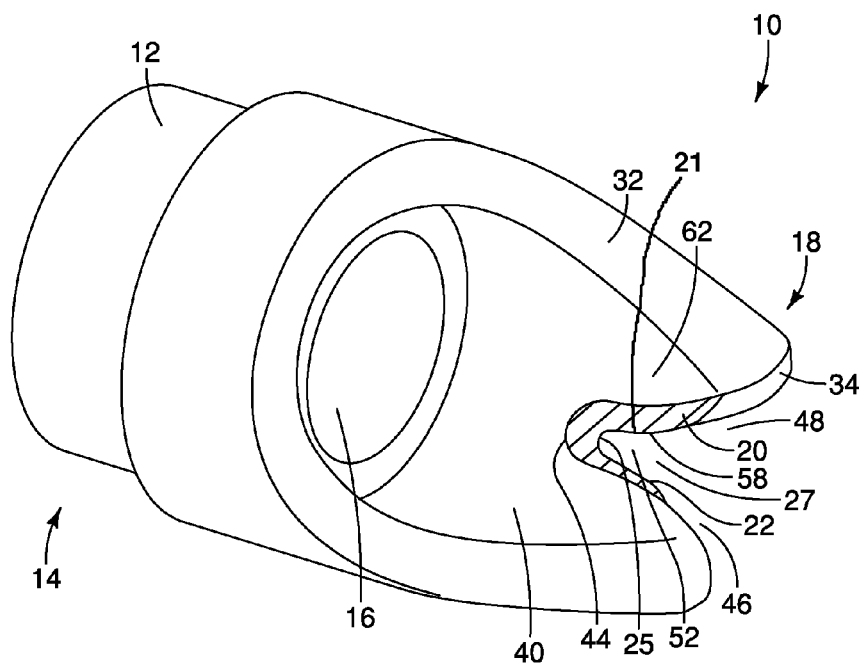
FIG. 1 is a perspective view showing a first side of an tissue cutting cap in accordance with an embodiment of the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the tissue cutting cap to a patient. Hence the term "distal" means the portion of the tissue cutting cap that is farthest from the physician and the term "proximal" means the portion of the tissue cutting cap that is nearest to the physician.

Figure 2:
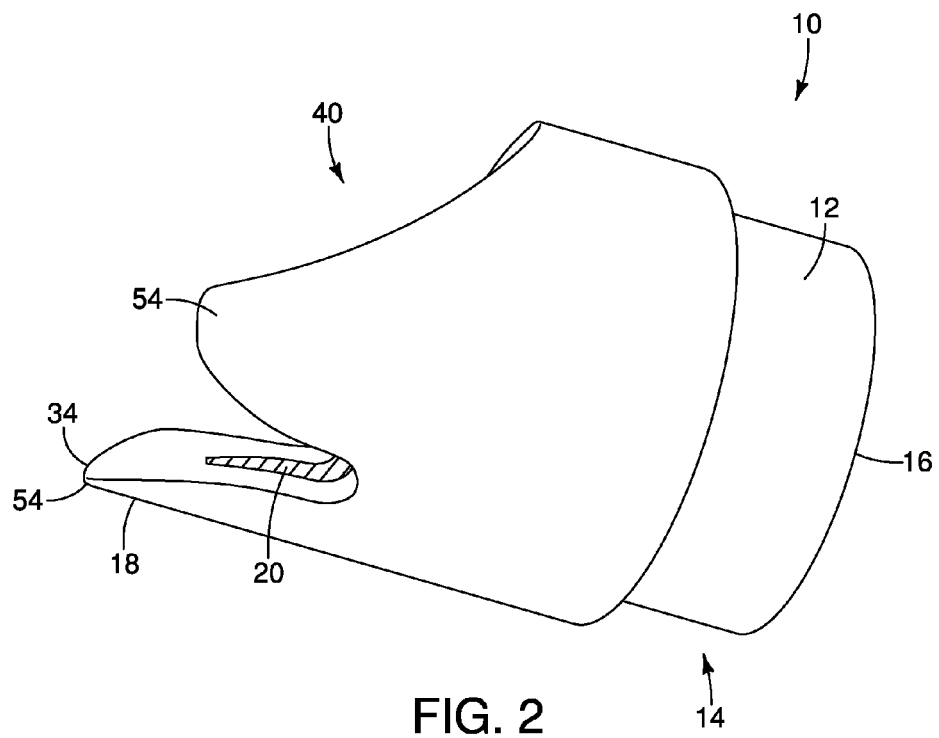
FIG. 2 is a perspective view showing a second side of the tissue cutting cap shown in FIG. 1.
Figure 3A:
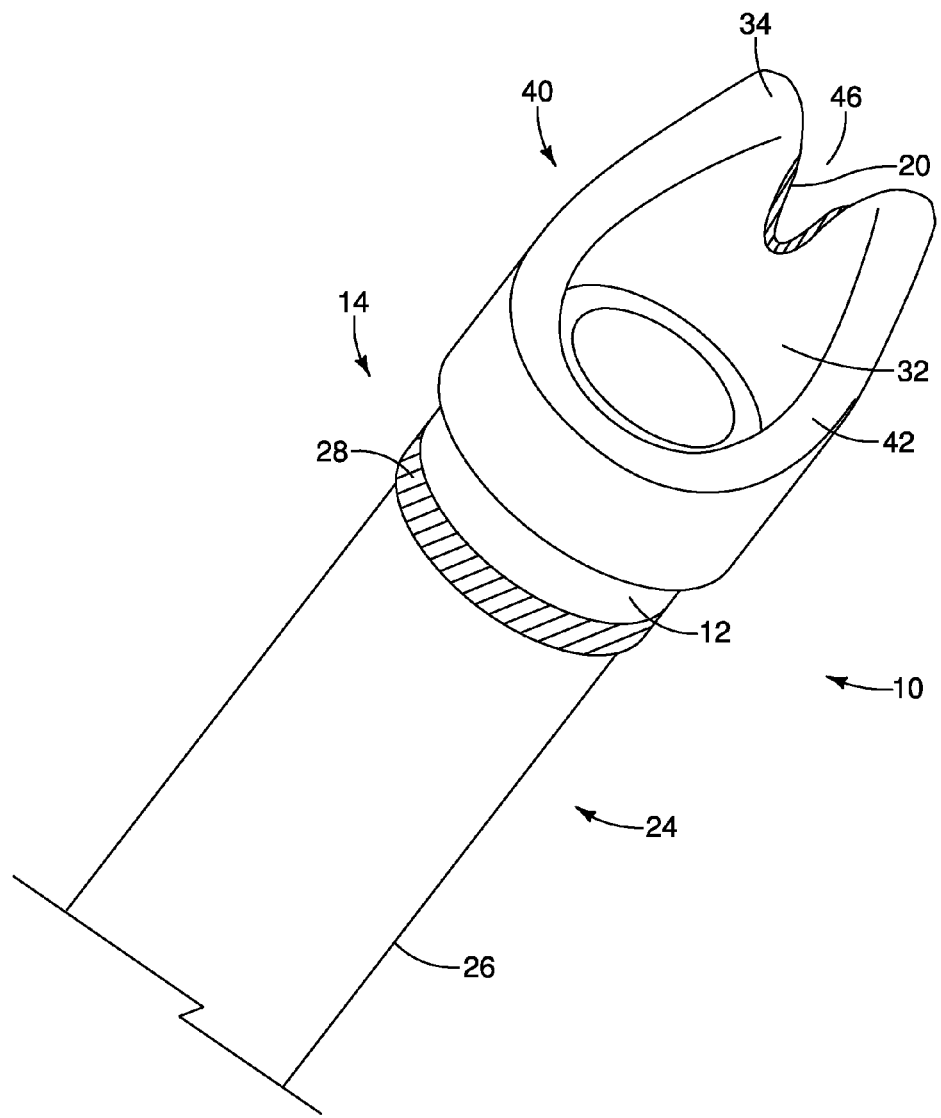
FIG. 3A is a perspective view of an embodiment of a tissue cutting cap positioned on a distal end of an endoscope.

FIGS. 1 and 2 illustrate an embodiment of a tissue cutting cap 10 in accordance with the present invention. As shown in FIGS. 1 and 2, the tissue cutting cap 10 includes a generally tubular body 12 at a proximal portion 14 of the cap 10 and having a lumen 16 formed therein. The ablation cap 10 includes a distal portion 18 having a cutting portion 20. The proximal portion 14 of the cap 10 is sized and shaped to fit over a distal end 24 of an endoscope 26 as shown in FIG. 3A. In some embodiments, the proximal portion 14 of the ablation cap 10 may include an elastomeric portion 28 that is connected to the tubular body 12 and that fits over the distal end 24 of the endoscope 26 to secure the cap 10 to the endoscope 26. In some embodiments, the proximal portion 14 may be made of a hard material that is sized and shaped to friction fit over the distal end 24 of the endoscope 26. In some embodiments, the cap 10 may be secured to the endoscope 26 using a band 80 shown in FIG. 3B that surrounds the proximal portion 14 of the cap 10 and a portion of the distal end 24 of the endoscope 26. The cap 10 may be positioned over the distal end 24 of the endoscope 26 and the band 80 may be pulled around the proximal portion 14 of the cap 10. As shown in FIG. 3B, the band 80 may include one or more openings 84 that are secured over one or more corresponding notches 86 on the proximal portion 14 of the cap 10. The band 80 may include a recessed portion 88 to fit against the proximal portion 14 of the cap 10 and a second portion 90 to fit against the distal end 24 of the endoscope 26 so that the cap 10 is secured to the endoscope 26. The band 80 may be tape, leather, elastomeric material or other material suitable for securing the cap 10 to the endoscope 26. The cap 10 may also be secured to the endoscope 26 using other methods, for example, using a hinged proximal portion that allows the proximal portion to open for attachment to the endoscope 26 and then be secured around the distal end of the endoscope 26 (not shown).

Figure 7:
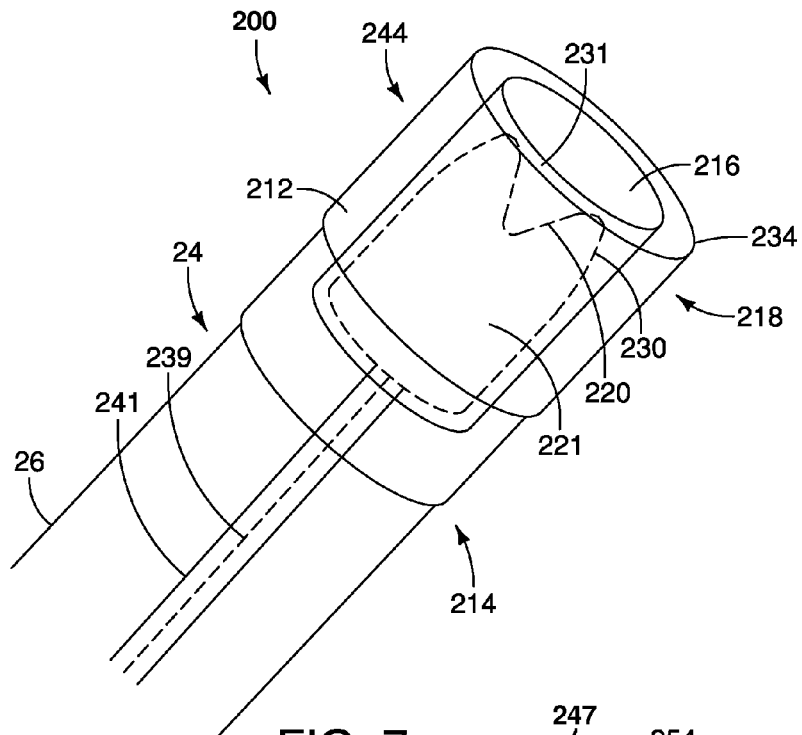
FIG. 7 is a perspective view of an alternative embodiment of a tissue cutting cap with the cutting portion recessed.

The distal portion 18 of the ablation cap 10 may extend beyond the distal end 24 of the endoscope 26. In some embodiments, the distal portion 18 may be formed from a material having sufficient transparency so that the operator using an optical port of the endoscope 26 may observe a portion of the tissue to be treated by viewing the tissue through the lumen 16 of the tubular body 12 or through a wall 32 of the distal portion 18 of the ablation cap 10. In some embodiments, the cap 10 or portions thereof may be clear, translucent or opaque or any combination thereof. The distal portion 18 may also include a portion that is formed from a material for magnifying the tissue under observation. In some embodiments, the distal portion 18 of the cap 10 does not extend 360° circumferentially around the cap 10 at a distal end 34 of the cap 10. In some embodiments as shown in FIGS. 1 and 2, the distal portion 18 may extend less than 180° of the circumference of the cap 10 and in some embodiments less than about 135°, or less than about 90°. In other embodiments, the distal portion 18 at the distal end 34 may extend 360° circumferentially around the cap 10 as shown in FIG. 7 and discussed in more detail below.

As shown in FIGS. 1 and 2, the cap 10 having a distal portion 18 extending less than 360° circumferentially around the cap 10 includes an open portion 40 defined by the wall 32 of the distal portion 18. The open portion 40 connects to the lumen 16 extending though the body 12 of the cap 10. The open portion 40 may be configured to allow tissue to be exposed to the cutting portion 20. An edge 42 of the wall 32 may be curvilinear to facilitate advancement of the cap 10 toward the tissue to be treated.

In some embodiments, the cutting portion 20 of the cap 10 may be recessed from the distal end 34 of the cap 10 so that the cutting portion 20 is proximal to the distal end 34 when the cutting portion 20 is exposed. The cutting portion 20 may include a first side 21, a second side 22 and an end portion 25. The first and second sides 21, 22 form an opening 27 into which the tissue to be cut can be inserted. The end portion 25 is generally opposite and proximal to the opening 27. As shown in FIG. 1, the cutting portion 20 may be v-shaped. In other embodiments, the cutting portion 20 may be u-shaped or polygonal-shaped or any other shape that allows specific layers of the tissue to be cut, but prevents perforation of the entire tissue. A proximal portion 44 of the cuffing portion 20 may be positioned distal to the distal end 24 of the endoscope 26 so that one or more medical devices may be extended distally from the endoscope 26 to facilitate manipulation of the tissue to be cut and to help position the tissue with respect to the cutting portion 20 as described in more detail below. The size of the cutting portion 20 may vary depending on the size of the tissue to be sampled, the size of the lumen from which the sample is cut, the size of the endoscope and the like. In some embodiments, the cutting portion may include at least one electrode. In some embodiments, the cutting portion may include a blade having a cutting edge.

The distal end 34 of the cap 10 includes an opening 46 in the wall 34 that is sized and shaped to accommodate the cutting portion 20. By way of non-limiting example, in some embodiments, the opening 46 may be v-shaped to accommodate a v-shaped cutting portion 20. A distal end 48 of the opening 46 may be wider than a proximal end 52 of the opening 48 to help facilitate cutting of the tissue. In some embodiments, the distal end 34 of the cap 10 adjacent to the opening 46 is provided with tips 54 on either side of the opening 46. In some embodiments, the tips 54 may be curvilinear to facilitate passage of the cap 10 through a body lumen. In some embodiments, the one or both tips 54 may be sharpened so that the tip 54 may penetrate the tissue to facilitate positioning the cutting portion 20 against the tissue. The wall 32 may surround and insulate the cutting portion 20.

Figure 4:
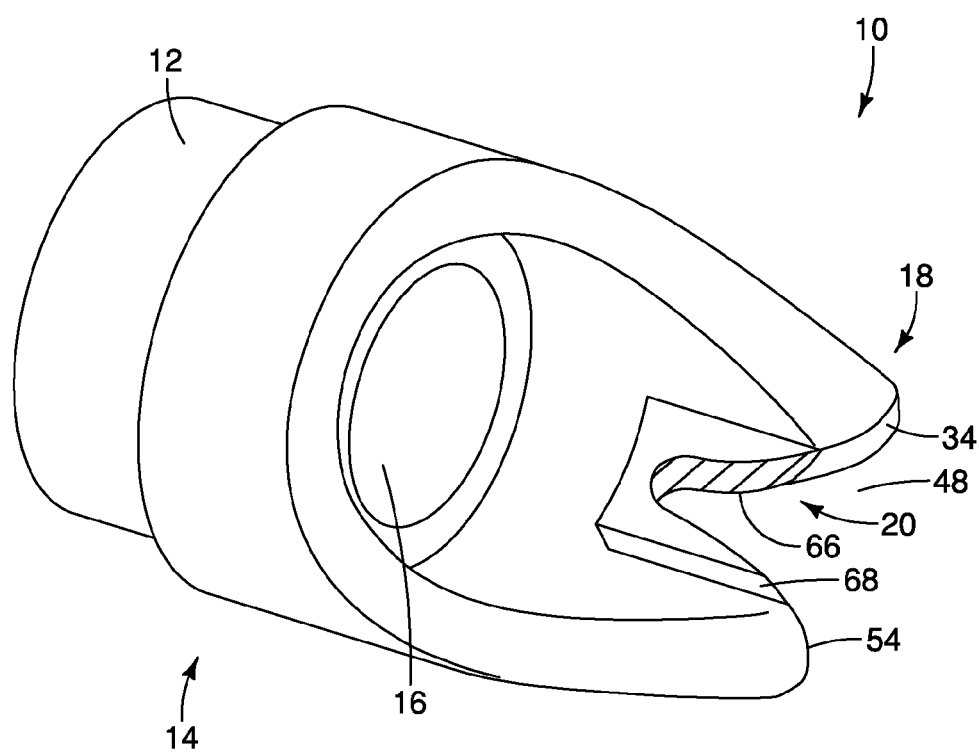
FIG. 4 is a perspective view of an embodiment of a tissue cutting cap.

In some embodiments, the cutting portion 20 includes at least one electrode and the cap 10 may operate as a monopolar device or a bipolar device. As shown in FIG. 1, the cutting portion 20 may be monopolar and a return pad (not shown) may be placed elsewhere on the patient. Alternatively, the cap 10 shown in FIG. 1 may be a bipolar device where the cutting portion 20 is an active electrode 58 and the cap 10 or a portion thereof is a return electrode 62. The cutting portion 20 may be provided as a blade having a cutting edge. As shown in FIG. 4, the cap 10 may be a bipolar device with an active electrode 66 at the base of the v of the cutting portion 20 and a return electrode 68 adjacent to the active electrode 66. The bipolar device would eliminate the need for a return pad and also may advantageously provide lower bleeding rates. The active (and return if bipolar) electrode(s) may be connected to one or more wires that extend from the electrode(s) to a connector that allows for connection to an electrosurgical unit or an active cord (not shown). The wire may be external to the endoscope 26 as shown in FIG. 7 or internal to the endoscope 26. In some embodiments, the cutting portion is sized to limit the amount of active cutting portion 20 that is exposed to the tissue so that the cutting portion 20 has an increased current density to cut the tissue rather than burn the tissue. When the cutting portion 20 is provided as a bipolar device, the surface area of the active portion is less than the surface area of the return portion to cut the tissue. In some embodiments, the exposed cutting portion 20 may be about 0.01-0.02 inches extending from the cap 10. Other sizes for the cutting portion may be used and will depend in part on the surface area of the cutting portion.

Figure 5:
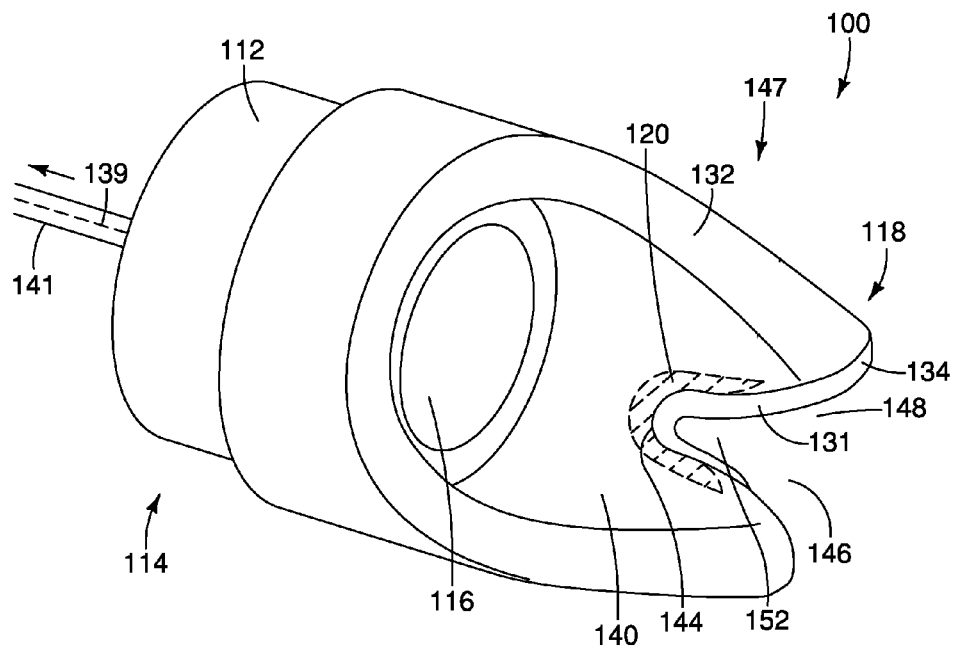
FIG. 5 is a perspective view of an embodiment of a tissue cutting cap with the cutting portion recessed within the body.
Figure 6:
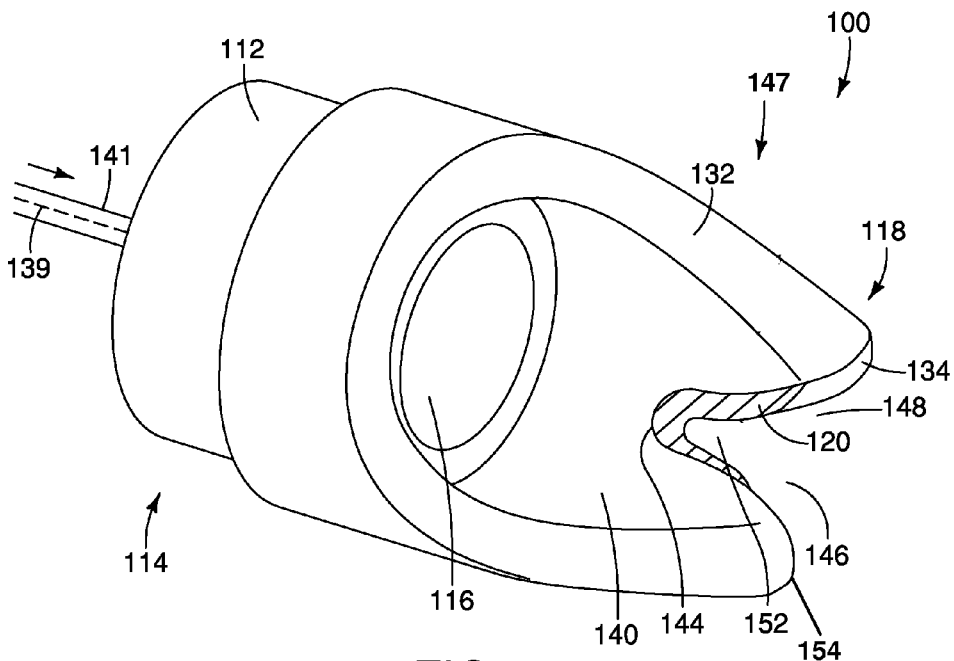
FIG. 6 is a perspective view of the embodiment of the tissue cutting cap shown in FIG. 5 with the cutting portion exposed.

FIGS. 5 and 6 illustrate an embodiment of a tissue cutting cap 100 in accordance with the present invention. The tissue cutting cap 100 is similar to the cap 10 described above with the exception that the cap 100 includes a cutting portion 120 that is movably positionable relative to a generally tubular body 112 of the cap 100. The shape of the cutting portion 120 is similar to the shape of the cutting portion 20 described above. Similar to the tissue cutting cap 10, described above, the tissue cutting cap 100 includes a proximal portion 114 and a distal portion 118. A lumen 116 extends through at least a portion of the body 112. The proximal portion 114 of the cap 100 is sized and shaped to fit over a distal end 24 of an endoscope 26 and may be secured to the endoscope 26 similar to the cap 10 as described above.

The distal portion 118 of the ablation cap 100 may extend beyond the distal end 24 of the endoscope 26. In some embodiments, the distal portion 118 may be formed from a material having sufficient transparency so that the operator using an optical port of the endoscope 26 may observe a portion of the tissue to be treated by viewing the tissue through the lumen 116 of the tubular body 112 or through a wall 132 of the distal portion 118 of the ablation cap 100. In some embodiments, the cap 100 or portions thereof may be dear, translucent or opaque or any combination thereof. The distal portion 118 may also include a portion that is formed from a material for magnifying the tissue under observation. Similar to the cap 10, the distal portion 118 of the cap 100 may extend less than 360° circumferentially around the cap 100 at a distal end 134 of the cap 100.

As shown in FIGS. 5 and 6, the cap 100 having a distal portion 118 extending less than 360° circumferentially around the cap 100 includes an open portion 140 defined by the wall 132 of the distal portion 118. The open portion 140 connects to the lumen 116 extending though the body 112 of the cap 100. The open portion 140 may be configured to allow tissue to be exposed to the cutting portion 120 when the cutting portion 120 is extended distally from the body 112. An edge 158 of the wall 132 may be curvilinear to facilitate advancement of the cap 100 toward the tissue to be treated.

The cutting portion 120 is movably positional relative to the body 112. As shown in FIG. 5, the cutting portion 120 is positioned within a recess 131 formed in the body 112. In some embodiments, the cutting portion 120 may be entirely withdrawn in to the recess 131 of the body 112 in a recessed position 144. The cutting portion 120 may be connected to a drive catheter 141 that extends proximally from the cutting portion 120 to a proximal control handle (not shown). The drive catheter 141 is distally movable to extend the cutting portion 120 from the recess 131 in a cutting configuration 147 as shown in FIG. 6 and proximally movable to reposition the cutting portion 120 within the recess 131 as shown in FIG. 5. Typically, the cutting portion 120 is positioned within the recess 131 when the tissue cutting cap 100 is being delivered to a treatment site or being repositioned within a patient's lumen for additional treatment at one or more additional sites. Positioning of the cutting portion 120 within the recess 131 also helps to prevent accidental energy delivery, for example to healthy tissue. The cutting portion 120 is at least partially distally extended from the recess 131 for treatment at a site and energy is delivered to the tissue to ablate the diseased tissue as described in more detail below. The cutting portion 120 may be configured for monopolar or bipolar energy delivery as discussed above with reference to the cap 10. One or more wires 139 may extend from the cutting portion 120 to a connector (not shown) for connection to an electrosurgical unit or active cord (not shown) and may co-extend with the drive catheter 141. In some embodiments, the drive catheter 141 and/or the wires 139 are positioned external to the endoscope 26. In some embodiments, the drive catheter 141 and/or the wires 139 extend within a channel of the endoscope 26.

Similar to the embodiment of the tissue cutting cap 10, the cutting portion 120 of the cap 100 may be recessed from the distal end 134 of the cap 100 when the cutting portion 120 is in the cutting configuration 147 shown in FIG. 6 so that the cutting portion 120 is proximal to the distal end 134. As shown in FIG. 6, the cutting portion 120 may be v-shaped. In other embodiments, the cutting portion 120 may be u-shaped or polygonal-shaped or other shape that allows specific layers of the tissue to be cut, but prevents full-thickness cutting of the tissue. The cutting portion 120 may be sized and shape similarly to the cutting portion 20 described above. A proximal portion 144 of the cutting portion 120 may be positioned distal to the distal end 24 of the endoscope 26 so that one or more medical devices may be extended distally from the endoscope 26 to facilitate manipulation of the tissue to be cut and to help position the tissue with respect to the cutting portion 120 as described in more detail below. The size of the cutting portion 120 may vary depending on the size of the tissue to be sampled, the size of the lumen from which the sample is cut, the size of the endoscope and the like.

Similar to the cap 10, the distal end 134 of the cap 100 includes an opening 146 in the wall 134 that is sized and shaped to accommodate the cutting portion 120. The opening 146 may be sized and shaped according to the size and shape of the cutting portion 120 positioned within the opening 146. A distal end 148 of the opening 146 may be wider than a proximal end 152 of the opening 148 to help facilitate cutting of the tissue. In some embodiments, the distal end 134 of the cap 100 adjacent to the opening 146 is provided with tips 154 on either side of the opening 146. In some embodiments, the tips 154 may be curvilinear to facilitate passage of the cap 100 through a body lumen. In some embodiments, the one or both tips 154 may be sharpened so that the tip 154 may penetrate the tissue to facilitate positioning the cutting portion 120 against the tissue. The wall 132 may surround and insulate the cutting portion 120.

Figure 8:
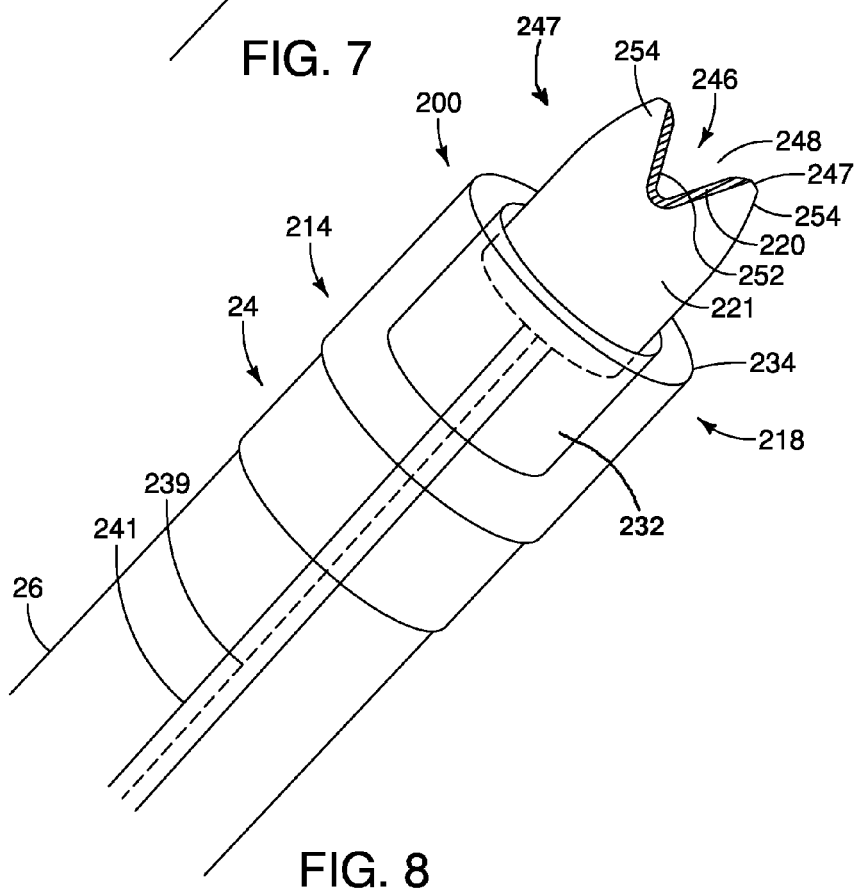
FIG. 8 is a perspective view of the embodiment of the tissue cutting cap shown in FIG. 7 with the cutting portion exposed.

FIGS. 7 and 8 illustrate an embodiment of a tissue cutting cap 200 in accordance with the present invention. The tissue cutting cap 200 is similar to the embodiments described above with the exception that the cap 200 includes a cutting portion 220 that is movably positionable relative to a generally tubular body 212 of the cap 200 and is extendable from a cover portion 230 of the cap 200. Similar to the tissue cutting cap embodiments described above, the tissue cutting cap 200 includes a proximal portion 214 and a distal portion 218. A lumen 216 extends through the body 212. The proximal portion 214 of the cap 200 is sized and shaped to fit over a distal end 24 of an endoscope 26 and may be secured to the endoscope 26 similar to the cap 10 as described above.

The distal portion 218 of the ablation cap 200 may extend beyond the distal end 24 of the endoscope 26. In some embodiments, the distal portion 218 may be formed from a material having sufficient transparency so that the operator using an optical port of the endoscope 26 may observe a portion of the tissue to be treated by viewing the tissue through the lumen 216 of the tubular body 212 or through a wall 232 of the distal portion 218 of the ablation cap 200. In some embodiments, the cap 200 or portions thereof may be clear, translucent or opaque or any combination thereof. The distal portion 218 may also include a portion that is formed from a material for magnifying the tissue under observation. As shown in FIG. 7, the distal portion 218 of the cap 200 may extend 360° circumferentially around the cap 200 at a distal end 234 of the cap 200.

The tissue cutting cap 200 may further include the cover portion 230 that includes a recess 231 formed as part of the cap 200. The cover portion 230 may be integrally formed with the cap 200 or provided as a separate portion and connected to the cap 200. The cover portion 230 is at least partially spaced apart from the tubular body 212 to form the recess 231. The recess 231 may be sized and shaped to hold an extendable cutting portion 220 within the recess 231 in a covered position 244 as shown in FIG. 7 so that the cutting portion 220 is proximal to a distal end 234 of the tissue cutting cap 200. The cutting portion 220 is slidably positionable within the recess 231 of the cover portion 230 and may be completely covered by the cover portion 230. As shown in FIG. 8, the cutting portion 220 may be extended distally from the recess 231 so that at least a portion of the cutting portion 220 is exposed and can contact the tissue to be treated. The cutting portion 220 may be mounted in a slider member 221 that supports the cutting portion 220. The slider member 221 may be curved and may include an opening 246 in a distal end 247 of the slider member 221 that is sized and shaped to accommodate the cutting portion 220. Similar to the cap 10 described above, the cutting portion 220 may be v-shaped, u-shaped or polygonal and the like, and the opening 246 may be similarly shaped to accommodate the shape of the cutting portion 220. A distal end 248 of the opening 246 may be wider than a proximal end 252 of the opening 248 to help facilitate cutting of the tissue. In some embodiments, the distal end 247 of the slider member 221 adjacent to the opening 246 is provided with tips 254 on either side of the opening 246. In some embodiments, the one or both tips 254 may be sharpened so that the tip 254 may penetrate the tissue to facilitate positioning the cutting portion 220 against the tissue.

As discussed above, the cutting portion 220 on the slider member 221 is movably positional relative to the body 212. As shown in FIG. 7, the cutting portion 220 and the slider member 221 are positioned within the recess 231 formed in the body 212. In some embodiments, the cutting portion 220 may be entirely withdrawn in to the recess 231 of the body 212 in a recessed position 244 shown in FIG. 7. The slider member 221 may be connected to a drive catheter 241 that extends proximally from the slider member 221 to a proximal control handle (not shown). The drive catheter 241 is distally movable to extend the slider member 221 and the cutting portion 220 from the recess 231 in a cutting configuration 247 as shown in FIG. 8 and proximally movable to re-position the cutting portion 221 within the recess 231 as shown in FIG. 7. Typically, the cutting portion 220 and the slider member 221 are positioned within the recess 231 when the tissue cutting cap 200 is being delivered to a treatment site or being repositioned within a patient's lumen for additional treatment at one or more additional sites. Positioning of the cutting portion 220 within the recess 231 also helps to prevent accidental energy delivery, for example to healthy tissue. The cutting portion 220 is at least partially distally extended from the recess 231 for treatment at a site and energy is delivered to the tissue to ablate the diseased tissue as described in more detail below, The cutting portion 220 may be configured for monopolar or bipolar energy delivery as discussed above with reference to the cap 10 and may be sized and shaped similar to the cutting portion 20. One or more wires 239 may extend from the cutting portion 220 to a connector (not shown) for connection to an electrosurgical unit or active cord (not shown) and may co-extend with the drive catheter 241. In some embodiments, the drive catheter 241 and/or the wires 239 are positioned external to the endoscope 26. In some embodiments, the drive catheter 241 and/or the wires 239 extend within a channel of the endoscope 26.

In some embodiments, the tissue cutting cap may be made primarily of a substantially transparent or translucent polymer such as polytetrafluorothylene (PTFE). Additional possible materials include, but are not limited to the following, polyethylene ether ketone (PEEK), fluorinated ethylene propylene (FEP), perfluoroalkoxy polymer resin (PFA), polyamide, polyurethane, high density or low density polyethylene, and nylon. In some embodiments, the tissue cutting cap may be formed from a lubricious material such as PTFE and the like for easy slidability within the patient's lumen for delivery to the treatment site. In some embodiments, the tissue cutting cap or a portion thereof may be formed from magnifying or other image enhancing materials. The tissue cutting cap or a portion thereof may also be coated or impregnated with other compounds and materials to achieve the desired properties. Exemplary coatings or additives include, but are not limited to, parylene, glass fillers, silicone hydrogel polymers and hydrophilic coatings. The tissue cutting cap or portions thereof may be made of different durometers of material. By way of non-limiting example, the tissue cutting cap or a distal portion thereof may be made of a softer material to allow for easier advancement of the cap to the target tissue site.

Figure 9:
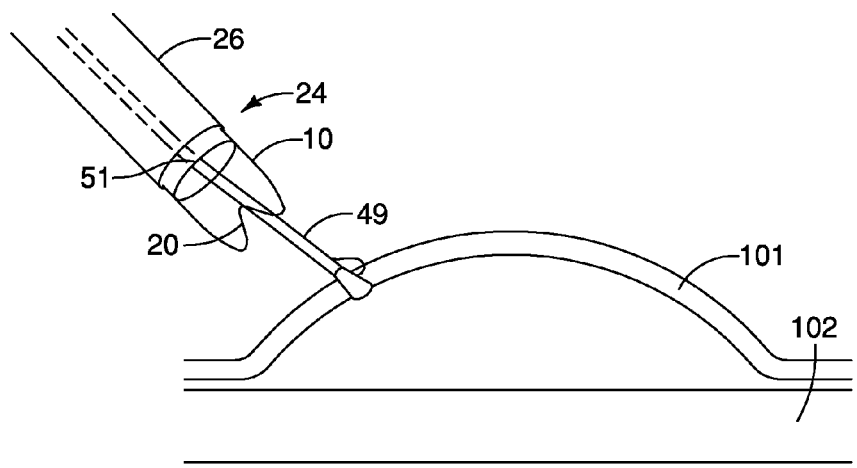
FIGS. 9-11 illustrate operation of an embodiment of a tissue cutting device.
Figure 10:
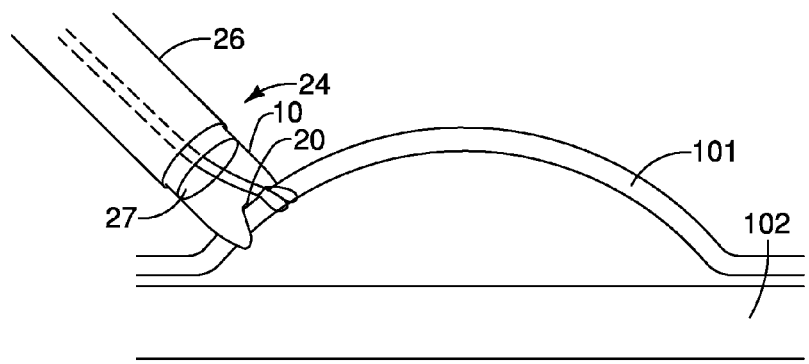
Figure 11:

Operation of the tissue cutting cap using the tissue cutting cap 10 as a non-limiting example will be explained with reference to FIGS. 9-14. FIGS. 9 and 10 illustrate the tissue cutting cap 10 positioned on the distal of end 24 of the endoscope 26 that is been positioned near a tissue treatment site, As shown in FIG. 9, a forceps device 49 is extended distally from a working channel 51 of the endoscope 26. The forceps device 49 grasps a first layer of tissue 101 and pulls the first layer of tissue 101 away from a second layer of tissue 102. The layers 101, 102 may be any adjacent layers of tissue, for example, the muscularis and submucosal layers. As shown in FIG. 10, the cutting portion 20 of the cap 10 is advanced to the first layer of tissue 101 and power is supplied to the cutting portion 20 so that the cutting portion 20 cuts the first tissue layer 101 and leaves the second layer 102 intact. A sample of the first tissue layer 101 may be cut away from and removed from the second tissue layer 102. The forceps 49 may be used to hold onto the first tissue layer 101 as the layer 101 is being cut and to remove the sample of the first tissue layer 101 for testing. For example, in some embodiments, the forceps 49 may be proximally withdrawn from the site after the first tissue layer 101 has been cut away from the second tissue layer 102 so that the forceps 49 delivers the tissue 101 to the physician. In some embodiments, the endoscope 26 may include a suction port 27 to facilitate removal of the tissue 101 and/or to facilitate elevation of the first layer of tissue 101 away from the second tissue layer 102 to facilitate cutting with the cutting portion 20. FIG. 11 illustrates the site after the first tissue layer 101 has been removed and the second tissue layer 102 remains intact.

Figure 12:
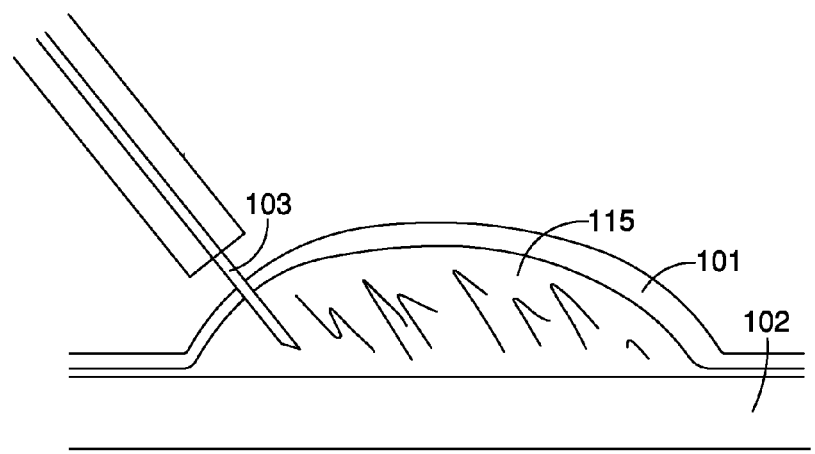
FIGS. 12-14 illustrate operation of an embodiment of a tissue cutting device.
Figure 13:
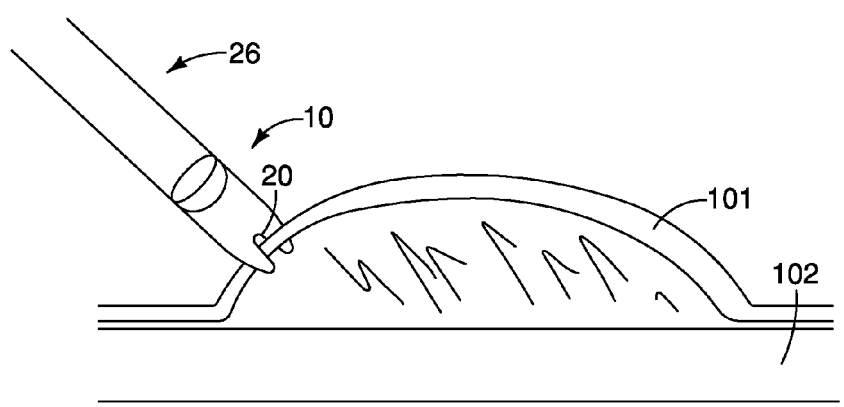
Figure 14:
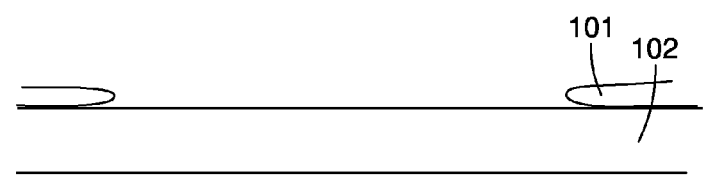

FIGS. 12-14 illustrate an alternative method of operation of the device 10. As shown in FIG. 12, a needle 103 is extended distally and inserted between the first tissue layer 101 and the second tissue layer 102. As shown in FIG. 12, the injection of the solution between the first tissue layer 101 and the second tissue layer 102 forms a fluid-filled pocket 115 that forces separation between the first and second tissue layers 101, 102, breaking the attachments between the tissue layers 101, 102. The elevated portion of the first tissue layer 101 may then be resected by the physician using the cutting portion 20 of the cap 10 as shown in FIG. 13. The cutting portion 20 of the cap 10 is advanced to the first layer of tissue 101 and power is supplied to the cutting portion 20 so that the cutting portion 20 cuts the first tissue layer 101 and leaves the second layer 102 intact. A sample of the first tissue layer 101 may be cut away from and removed from the second tissue layer 102. Similar to the method described with reference to FIGS. 9-11, the sample of the first tissue layer 101 may be removed by forceps or suction. The first tissue layer 101 is removed and the second tissue layer 102 remains intact as shown in FIG. 13.FIG. 14 illustrates the site after the first tissue layer 101 has been removed and the second tissue layer 102 remains in position at the site.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A tissue cutting cap comprising:
a body having a proximal portion, a distal portion, a distal end, and a lumen extending at least partially therethrough, the body having an opening formed in a wall of the body, the wall of the body extending at least partially circumferentially around the body and the opening extending from the distal end inward to the distal portion in the circumferentially extending portion of the wall;
a cutting portion operably connected to the body and positioned at least partially within the opening in the wall of the body so that the entire cutting portion is offset from a central longitudinal axis of the body, the cutting portion being positioned proximal to the distal end of the body so that the entire cutting portion does not extend distal to the distal end of the body, the cutting portion having a first side, a second side, an end operably connecting the first side and the second side and an opening defined by the first side and the second side, the end of the cutting portion being positioned proximal to a distal end of the first side of the cutting portion, the cutting portion opening being adapted to receive tissue to be cut therein;
wherein the proximal portion of the body is sized and shaped to fit on a distal end of an endoscope and the distal portion of the body is adapted to extend distal to a distal end of an endoscope.

2. The tissue cutting cap of claim 1, wherein the cutting portion is bipolar.

3. The tissue cutting cap of claim 1, wherein the cutting portion comprises an active electrode and at least a portion of the body comprises a return electrode.

4. The tissue cutting cap of claim 1, wherein the end of the cutting portion comprises an active electrode and a side of the cutting portion comprises a return electrode.

5. The tissue cutting cap of claim 1, wherein the cutting portion is v-shaped or u-shaped.

6. The tissue cutting cap of claim 1, wherein at least a portion of the body comprises a transparent material, a translucent material, a magnifying material or combinations thereof.

7. The tissue cutting cap of claim 1, wherein the cutting portion comprises at least one electrode.

8. The tissue cutting cap of claim 1, wherein the distal end of the body comprises a tip.

9. The tissue cutting cap of claim 8, wherein the tip includes a sharpened portion configured to initially penetrate tissue at a treatment site.

10. The tissue cutting cap of claim 1, wherein the cap is removably secured to an endoscope with an elastomeric portion or a band.

11. The tissue cutting cap of claim 1, wherein a distal end of the body opening is wider than a proximal end of the body opening.

12. The tissue cutting cap of claim 1, wherein the body opening is v-shaped or u-shaped.

13. The tissue cutting cap of claim 1, wherein a distal portion of the wall extends less than 360° circumferentially around the body.

14. The tissue cutting cap of claim 1 wherein an edge of the wall is curvilinear.

* * * * *